United States Patent
Platz

Patent Number: 5,264,640
Date of Patent: Nov. 23, 1993

[54] DEPOLYMERIZATION METHOD FOR RESOURCE RECOVERY FROM POLYMERIC WASTES

[75] Inventor: Gerald M. Platz, Conroe, Tex.

[73] Assignees: S-P Reclamation, Inc., Houston, Tex.

[21] Appl. No.: 864,426

[22] Filed: Apr. 6, 1992

[51] Int. Cl.⁵ .............. C07C 4/04; C07C 4/06
[52] U.S. Cl. .................... 585/241; 201/2.5; 241/DIG. 37; 264/28; 264/349; 264/DIG. 69; 264/130; 264/83; 425/DIG. 44
[58] Field of Search .............. 264/28, 101, 102, 349, 264/DIG. 69, 83, 130; 241/DIG. 37; 425/DIG. 44; 585/241; 201/2.5

[56] References Cited

U.S. PATENT DOCUMENTS

| | | | |
|---|---|---|---|
| 4,025,990 | 5/1977 | Lovette, Jr. | 241/DIG. 37 |
| 4,029,550 | 6/1977 | Mitsui et al. | |
| 4,051,212 | 9/1977 | Grigat et al. | 264/DIG. 69 |
| 4,098,649 | 7/1978 | Redker | 264/DIG. 69 |
| 4,240,587 | 12/1980 | Letsch | 241/DIB. 37 |
| 4,250,158 | 2/1981 | Solbakken et al. | 585/241 |
| 4,458,095 | 7/1984 | Wingfield, Jr. et al. | 585/241 |
| 4,515,659 | 5/1985 | Wingfield, Jr. et al. | 585/241 |
| 4,740,270 | 4/1988 | Roy . | |
| 4,746,406 | 5/1988 | Timmann | 585/241 |
| 4,863,106 | 9/1989 | Perkel | 241/DIG. 37 |
| 5,084,141 | 1/1992 | Holland | 505/241 |

FOREIGN PATENT DOCUMENTS 47-30107  8/1972  Japan .................. 264/DIG. 69

*Primary Examiner*—Jeffery Thurlow
*Assistant Examiner*—Mathieu Vargot
*Attorney, Agent, or Firm*—Arnold, White & Durkee

[57] ABSTRACT

Scrap rubber chunks from used tires are processed and the monomeric chemicals from which the tire rubber was synthesized are recovered. Rubber chunks reduced to a finely divided size are exposed to gaseous ozone to break down the cross-linked structure of the rubber. Subsequent thermal depolymerization occurs in a reactor chamber. Finely divided silica is introduced within the reactor to prevent agglomeration of rubber particles and to enhance the maintenance of a uniform reactor temperature. Reduced pressure within the reactor permits rapid removal of monomer vapors. Once the monomer vapors are separated, silica and carbon residues are recovered separately for either recycle or disposal.

24 Claims, 4 Drawing Sheets

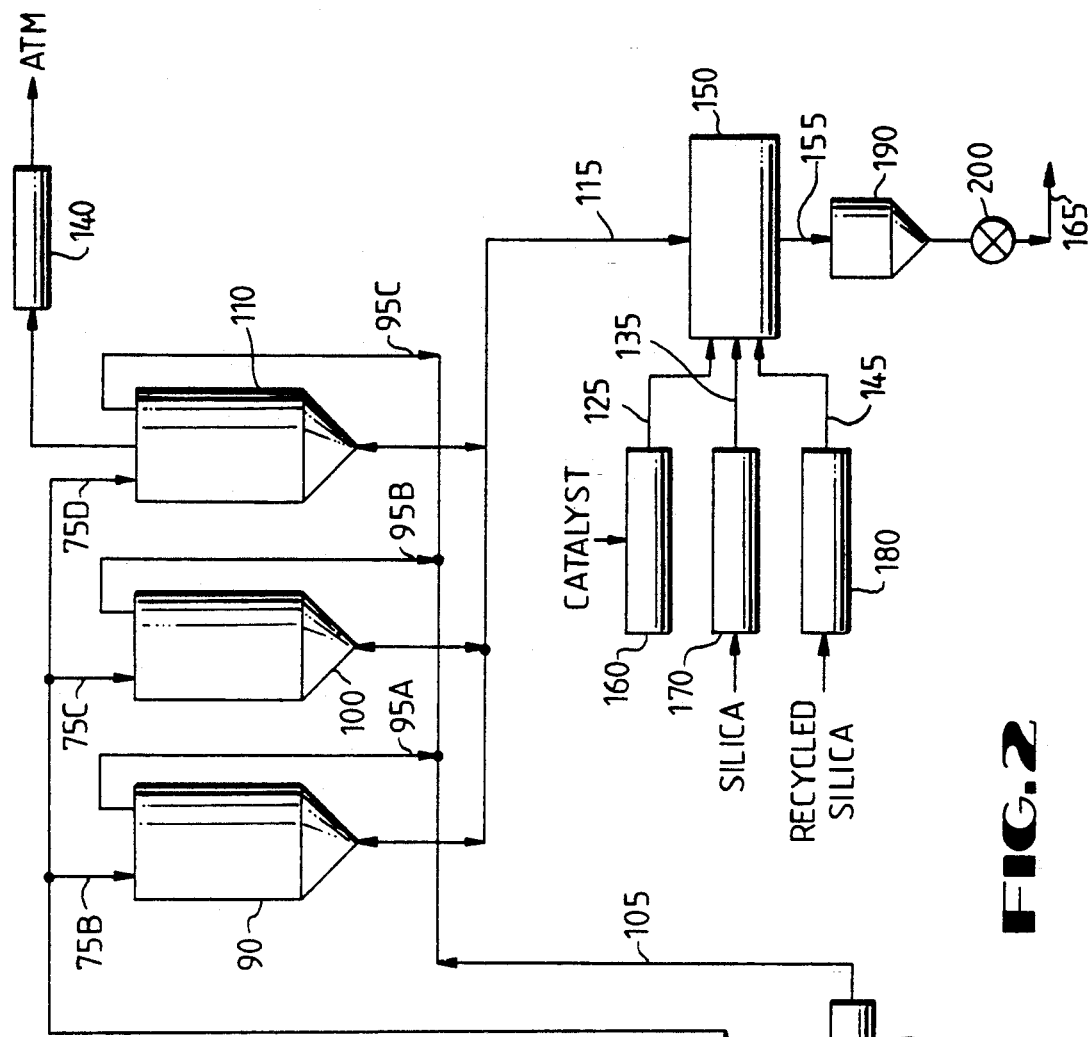
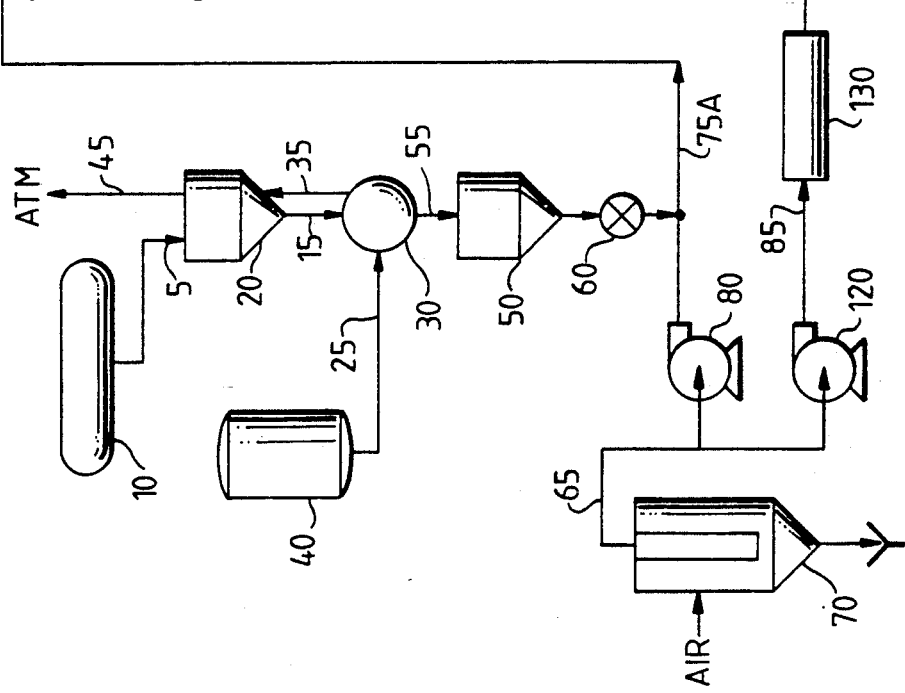
FIG. 2

DEPOLYMERIZATION METHOD FOR RESOURCE RECOVERY FROM POLYMERIC WASTES

BACKGROUND OF THE INVENTION

1. Field of the Invention

The present invention relates to a depolymerization process for recovering the original monomers from which polymerized products such as scrap or waste tires, rubber and plastics were created. Although reference is made in this application primarily to scrap tires and the recovery of monomers therefrom, it should be understood that a number of different polymerized products can substitute for the scrap tires referenced herein.

Each year approximately 240 million used tires are discarded. The vast majority of these used tires are put into landfills or, all too often, are disposed of illegally. Such disposal of scrap tires in landfills is becoming increasingly undesirable as significant environmental and social problems are associated with such activity. The availability of landfill space is diminishing, and there has been a national trend toward more stringent regulatory requirements on landfills. Hence, a considerable amount of attention has been devoted recently toward finding alternative uses for and methods of reclaiming scrap tires.

Some research and commercial efforts have been directed toward the development of new uses for old tires. Unprocessed used tires have been used in playgrounds, flower planters, and shoe soles, and tire pieces have been used as gaskets, shims, dock bumpers and shock absorbers. The use of processed used tires in road construction is also gaining some attention. Paving materials made from a combination of crumb rubber and asphalt may last up to three times as long as standard paving materials. However, because of the high costs associated with the use of scrap tires for roads, this approach has not gained wide acceptance. Studies continue to explore this use of scrap tires in addition to the somewhat more conventional use of tires as crash barriers and impact absorbers around highway and bridge abutments. However, these new uses for used tires only consume a minor portion of the annual accumulation of scrap tires.

Consequently, significant research and commercial activity has been directed toward development of the use of scrap tires as an energy source. The 240 million used tires discarded each year represent upwards of $7 \times 10^{13}$ BTU's of energy. Two approaches to tapping this energy source have received most of the attention. In the first, either whole or shredded tires alone are burned for fuel in incinerators or specially designed boilers, in many cases to generate electricity, or are added directly to cement kilns. In many tire incinerators combustion is not complete, resulting in the discharge of smoke and objectionable odors. Meeting federal emissions regulations for any combustion system is costly. In the second approach, tires have the steel belts removed by extensive shredding and are then combined with wood, paper pulp, or other refuse to get a fuel blend that can be burned to provide energy. While the combination of tires with other materials results in a higher total average BTU content for burning as compared to the other materials alone, difficulty in handling, which typically includes special feeding and blending equipment, makes this second approach a rather unattractive method for reclaiming scrap tires. Moreover, for some the incineration of waste plastics has been used to recover their BTU value, identical to the use of scrap tires as fuel.

While such approaches might seem attractive given rising natural-gas and fuel-oil costs, one major drawback to the approach is that valuable basic chemical building blocks or monomers, such as styrene, instead of being recovered, are consumed. The cost of these destroyed or lost monomers includes the costs, in energy and finite natural hydrocarbon resources, of exploration and drilling for new oil and the costs of transporting the crude oil and converting it to the intermediate chemicals from which rubber is made. Ethylene, propylene, butadiene, and styrene are a few examples of monomers derived from petrochemical sources and used in tire manufacture. The total energy required to make the monomers in the tire is on the order of 60,000 BTU per lb. The fuel energy value of a tire is approximately 15,000 BTU per lb. The cost to the environment of using the valuable monomers as fuel, rather than reclaiming and recycling them, would include the costs of the energy and finite natural resources used to make them, which are permanently lost, versus the relatively meager amount of energy and no natural resources recovered when they consumed. In addition, the costs to the environment of replacing rather than reclaiming the monomers includes the burden of the additional carbon dioxide generated by the energy used in replacement. Carbon dioxide, according to many studies, contributes to global warming. Thus, given the drawbacks associated with these uses for scrap tires, there has been a search for alternative uses for scrap tires that are less costly and that have minimal adverse impact on the environment.

Tires generally consist of rubber, carbon black, steel, fabric and other additives. Styrene-butadiene rubber is most commonly used in tire manufacturing, usually in combination with other elastomers such as natural rubber and ethylene propylene diene monomer (EPDM). Carbon black is used in the manufacture of tires to strengthen the rubber and increase resistance to abrasion. Steel, fiberglass, or fabric in the form of cords or belts is also present for reinforcement in the majority of tires produced today. Finally, other additives, such as antioxidants and antiozonants, are used in the tire manufacturing process to inhibit rubber deterioration and slow aging.

Polymerization is the process in which individual monomers join together in large numbers to form a polymer molecule. Where two different monomers join to form a polymer chain, a copolymer is produced. There are two broad classes of polymers and copolymers based on their polymerization: Condensation polymers, such as polyesters, nylon, polycarbonates, and polyurethanes, are those whose polymerized form has a lower molecular weight than the sum of the monomers used to make it (the balance is generated as other chemicals such as methanol or glycols during polymerization). Addition, or chain-growth, polymers, such as polyethylene and polypropylene, are those whose polymerized form has the same molecular weight as the sum of the monomers used to make them. Addition, or chain-growth, polymers are made in specific conditions of temperature and pressure and in the presence of an initiator (a form of catalyst) in which the polymer chain is propagated, or 'zipped' together. Styrenebutadiene rubber, EPDM, and natural rubber, which are the polymers used in tire manufacture, are additive polymers.

There are basically two ways to break down a polymer: pyrolysis and depolymerization. Pyrolysis, also known as thermal cracking, is a process in which polymer molecules are heated until they fragment into several smaller, dissimilar, random-sized molecules. Pyrolysis typically results in the polymer molecules breaking down into a complex mixture of alcohols, hydrocarbons, and other molecules, none of which is an original monomer. Overall, the thermal conditions required for depolymerization are significantly milder than those associated with pyrolysis processes.

Depolymerization, the second way to break down a polymer, is essentially the opposite of polymerization. In the depolymerization of condensation polymers, prior art teaches several hydrolytic methods, such as glycolysis, methanolysis or hydrolysis, categorized by the depolymerization reactant used, such as glycol, methanol or water, respectively, wherein, under specific conditions of temperature and pressure and, sometimes, in the presence of a catalyst, the reactant is added to the polymer causing the polymer chain to separate into its original monomers. An example of these methods is the recycling of PET (polyethylene terephthalate) bottles by a methanolysis process which produces the raw material DMT (dimethyl terephthalate, a precursor to PET), and ethylene glycol. The DMT is then blended with virgin feedstock and FDA-acceptable polymers for food bottles are made. Hydrolytic depolymerization methods have not proven to be effective with addition polymers.

2. The Prior Art

While not limited solely to addition, or chain-growth, polymers, the present invention teaches a method for their depolymerization. The process specifically creates conditions of temperature and pressure and the presence of a catalyst to depropagate or depolymerize these polymers to their constituent monomers. The depolymerization temperature and pressure ranges for many types of polymers and copolymers of the monomers from which the tires are made are well documented in the technical literature. The thermodynamics for the depolymerization of polymers is elucidated in "Thermodynamics of Polymerization" by H. Sawada, published by M. Dekker, 1976. As explained by Sawada, each polymer will have different conditions for depolymerization. For example, polybutadiene depolymerizes in the 325° C. to 475° C. range, while a 75/25 polybutadiene/styrene copolymer depolymerizes in the 327° C. to 430° C. range. Generally, the temperatures involved in the depolymerization of the polymers and copolymers from which tires are made are in the 135° C. to 500° C. range. However, neither the technical literature nor prior patents teach a process for the depolymerization of additive polymers on a commercial basis.

Tires contain a number of different polymers blended together. Waste plastics from post-consumer wastes are generally mixed polymers unless hand or mechanical means of separating the various polymers are used. The present invention teaches a method of depolymerizing and recovering the monomers from each polymer in a mixture of polymers by a succession of reactors operating at different conditions of temperature and pressure. Prior art does not reveal a method for the sequential depolymerization of polymers in a single process.

The stress cracking of rubber by ozone has been known for decades. Ball and Youmans reported in Rubber Age 55, 481-3, 1944, that sheets of carbon black vulcanizates of tire tread cracked in 30 minutes in ozonized air at temperatures of 25 deg F., thus demonstrating that treatment with ozone gas will cause cleavage of vulcanized rubber molecular linkages. Baker and King in 1950 and Allison and Stanley in 1952 reported that stressed natural and synthetic rubbers relax when exposed to ozonized air. The inclusion of antioxidants and antiozonate chemicals in rubbers and polymers has been and is being practiced to suppress the deleterious effects of ozone and is well documented in prior art. The present invention teaches the use of ozone treatment to break down the cross-linked rubber making it more susceptible to thermal depolymerization thus using an otherwise 'undesirable' reaction to its advantage. While the deleterious effect of ozone on rubber and other polymers has been known for a considerable time, there is no readily available information that past investigators utilized ozone to beneficially enhance a depolymerization reaction process.

The cryogenic grinding of tires and other materials is taught in the prior art. Lovette, Jr. teaches in U.S. Pat. No. 4,025,990 a process for reclaiming rubber, metal and fabric from whole tires by cooling the tires in a cryogenic freezer to the embrittlement temperature, comminuting them in a comminution device and passing the resulting particles through a series of screening and density classification operations followed by magnetic material separation and further cryogenic size reduction to produce rubber crumb having a particle size of about 1/20 inch or less. Other inventors have proposed similar procedures to achieve particle size reduction. The cryogenic method illustrated in the present invention is a preferred embodiment of achieving reduced particle size but other methods may be used within the spirit and scope of the invention.

SUMMARY OF THE INVENTION

The principal objective of this invention is to provide an environmentally acceptable process whereby the hydrocarbon feedstocks, or monomers, from which polymers are made, can be recovered for reuse.

A further objective is apply depolymerization technology to cause the polymer molecule to break down into the molecules from which it was made.

It is a still further objective to combine the cryogenic grinding of polymers and the ozone degradation processes to enhance the depolymerization process.

An additional objective of this invention will be to employ multiple close coupled depolymerization reactors in series, each at different process conditions, to recover the respective monomers.

It is an objective of this invention to provide a process whereby the reclamation of waste polymers does not contribute pollutants to the atmosphere as does the combustion of tires to produce energy.

Another objective of this invention is to provide a process which will provide reusable monomers at a lower cost than the costs involved in manufacturing fresh monomer feedstocks from crude oil or natural gas reserves.

Another objective is to provide a process to provide reusable monomers to effect a net conservation of crude oil and natural gas reserves. Typically, the types of recovered monomers sought include: styrene, butadiene, propylene, ethylene, methyl methacrylate, isobutylene, benzene, methacrylic acid, methacrylonitrile, methyl styrene, to name a few.

These and other objects of the present invention are accomplished, in broad aspect, in a system for treating rubber tires, plastics, resins and related solid polymeric materials by first reducing the size of the materials by cyrogenic grinding methods and then treating the resulting particles with ozone to initially break down the vulcanized, or cross-linked, rubber and natural rubber making them more susceptible to thermal depolymerization. The ozone treated particles are fed into a reaction zone under conditions to depolymerize the polymeric constituents of the particles into the monomers from which the polymeric constituents were derived. It is contemplated that other products, notably carbon black, will be recovered with the monomers. However, the monomers are the products of principal interest. Typically, the monomer products are in the vapor or gas phase, and they are separated from the other products by a vacuum distillation system or by other conventional systems. Thus, they may be separated from the carbon black, unreacted rubber particles, and the like by passage through bag filters or other suitable separation means.

Cryogenic grinding of solids has been practiced for many years by numerous organizations. The principle involved is the chilling of coarse material to below its embrittlement temperature as the material is fed into the comminution equipment. The embrittlement must occur rapidly. The highest heat transfer, as well as the greatest heat transfer rate, occurs as the cryogen flashes or boils to a gas. Spraying the cryogen, such as liquid nitrogen, onto the conveyed solids has been found to provide the best cooling with the most efficient use of the cryogen. When the temperature of a polymer is reduced below its embrittlement temperature it will easily shatter when impacted to less than $-40$ mesh. In the preferred embodiment of this invention the feed into the cryogenic grinder is continuous. The comminution equipment, such as manufactured by the Fitzpatrick Company, includes internal perforated screens through which the final pulverized particles must pass, thus additionally allowing for uniform particle size range. The thermal embrittlement point of various polymers is well above the boiling point of the various cryogenic fluids contemplated, including liquid nitrogen, or dilute blends of liquid oxygen in liquid nitrogen, or other cryogenic fluids. Generally cryogenic temperatures in the range of $-196°$ C. to $-40°$ C. are contemplated with the preferred temperature being in the range of $-196°$ C. to $-76°$ C.

The objectives in reducing the size of the feed to the depolymerization process to a very small size are (1) to accomplish depolymerization of the particles immediately upon exposure to the reactor thermal conditions to minimize the opportunity for particles to soften and agglomerate, (2) to minimize the residence time of the particles in the reactor decreasing the opportunity for pyrolysis of the rubber and/or the depolymerized volatile matter and (3) to allow for the maximum surface area to be exposed to the ozone treatment. The desired size of the pulverized particles is dictated by the very poor thermal conductivity of polymers and rubbers. The particle size will continuously diminish as the polymer on the outer surface of the particles depolymerizes, exposing a fresh surface of polymer throughout the process. The smaller the initial size of the particles the shorter its residence time in the reactor, minimizing the opportunity for the softened polymer particles to agglomerate with other softened particles. With reduced residence time the size of the depolymerization reactor is reduced, thus favorably effecting capital costs. The embrittled rubber particles are shattered in the cryogenic grinder to very small sizes, of the order of $-45$ mesh U.S. sieve size. Generally the feed will have a particle size in the range of $-6$ to $+25$ mesh U.S. sieve screen. Preferably the feed will have particle size of $-12$ to $+14$ U.S. sieve screens.

The pulverized rubber particles are conveyed into an ozone treatment silo and are distributed within the silos so as to be readily penetrated by the ozone. An alternative embodiment of this invention contains multiple ozone treatment silos, each with its own bed of rubber particles. This application contemplates up to three such ozone treatment silos for illustrative purposes only. It will be understood, however, that the number of ozone treatment silos is not a limitation of this invention. This invention permits flexibility so that a user may tailor the process to a particular set of needs under a certain set of operating conditions. For example, additional ozone treatment silos may be used as storage silos for the rubber particle feedstock when the supply of such feedstock exceeds demand.

Air is filtered through a bag filter en route to an ozone generator where a portion of the oxygen in the air is converted to gaseous ozone. The concentration of gaseous ozone in the stream exiting the ozone generator may vary according to the demands of the process user. Generally, however, concentrations of about three parts per thousand by volume are contemplated.

The ozone-laden stream exits the ozone generator, enters the ozone treatment silo, and passes through the rubber particle bed and out of the silo. When multiple ozone treatment silos are connected in series, the ozone-laden stream passes out of one silo, into the next, through that silo's contents, out of that silo, and so on. The ozone-laden stream is finally directed through a hot copper oxide bed to destroy any ozone in the stream, and the stream is then vented to the atmosphere. In a preferred embodiment of this invention, both the bottom feed streams to the ozone treatment silos and the oxidizing streams vented from the top of the silos are valved and manifolded to permit the flow of the ozone-laden gas stream in any desired flow pattern.

Past attempts at thermal depolymerization of used tire rubber failed because thermal treatment of vulcanized or, as other wise known, cross-linked rubber by itself, was unable to rupture the chemical bonds of the cross-linked rubber. The conditions for depolymerization are relatively mild compared to those for pyrolysis. The conditions applied by other investigators were too severe causing thermal pyrolysis with the resultant decomposition of the rubber into less valuable products. The act of cross-linking joins small molecules together through available chemical bonding to form giant molecules having different physical properties. The exposure time of the rubber particles in the ozone atmosphere of the ozone treatment silos is sufficient to give the ozone time to rupture the chemical bonds of the rubber particles and thus make them vulnerable to depolymerization. The phenomena of cracking of rubber by ozone has received considerable attention in the technical world, establishing that relatively low concentrations of ozone in air causes the failure of stabilized rubber. The optimum exposure time of pulverized rubber particles to ozone for the beneficial use of its effects has not been established. However, based on existing information in the literature the exposure may range from two to 48 hours. The longer the exposure to ozone, the more complete the chemical breakdown of rubber will be. In the preferred embodiment of the invention, the exposure time of the pulverized rubber particles in the ozone treatment silos will be about 36 hours.

The ozone treated rubber particles are fed from the ozone treatment silos, preferably continuously, into a ribbon blender. Streams of catalyst, fresh silica, and hot recycled silica are also fed into the ribbon blender, again preferably continuously. In a preferred embodiment of this invention, the streams entering the ribbon blender are weighed so that the stream materials may be combined in desired proportions. The purpose of the catalyst, such as potassium carbonate, magnesium carbonate, calcium carbonate or sodium carbonate, is to enhance the chemical cleavage of the monomers from their polymer bonds. The purpose of the finely divided silica is to prevent agglomeration of molten rubber particles and to act as a temperature stabilizing influence in the reactor.

The blended depolymerization feed discharged from the ribbon blender enters a reactor feed silo. The blended depolymerization feed is then discharged into a depolymerization reaction section. Preferably, the discharge from the ribbon blender through the reactor feed silo and into the depolymerization reaction section is continuous.

In the depolymerization reaction section, the blended depolymerization feed is preferably depolymerized under vacuum and under thermal conditions sufficient to effect monomer vaporization. The vaporized monomers are fed through a bag filter to short path vacuum distillation system for recovery. Solids in the reactor are recovered and disposed of separately.

In a preferred embodiment of this invention a series of depolymerization reactors are present, each at a different operating temperature as required to recover different monomers. In a preferred embodiment, the first reactor in series operates at the lowest required temperature for a selected polymer, and successive reactors operate at successively higher temperatures, each such temperature being that required for a particular polymer. Each depolymerization reactor preferably comprises a custom designed, elongated, slightly inclined, rotating cylinder fitted with internal baffles that tumble the blended depolymerization feed as the reactor rotates. The residence time of solids within any given reactor is controlled by the reactor's rate of rotation. The overall operating temperatures of the reactors are typically in the range of 300° C. to 550° C. The reactor will be heated by external panel coils, circulating a heat exchange fluid appropriate for maintaining the desired reaction temperature. In the preferred embodiment, the reactor vacuum will be maintained by the same vacuum systems servicing the vacuum distillation unit. The reactors will be typically under a vacuum of approximately 27 inches of mercury.

As depolymerization takes place on the surface of the particulate, the monomers evolving vaporize and are immediately removed from the reactor by vacuum of the vacuum distillation unit to preclude their decomposing into less valuable products. Each reactor is preferably linked to a separate bag filter to remove entrained solids from the vaporized monomer stream. If the combination of recovered monomers permits, a single short path vacuum distillation unit, rather than a series of units, is preferred for recovery and separation of the monomers.

Recovery of the solids in the reactor takes place so as not to contaminate the monomers being recovered. Thus silica is separated out and routed back to the feed preparation section. Carbon black exits the reactor series combined with silica, sulfur, ash and any remaining non-volatized hydrocarbons or other residue thus constituting a char. Said char can be disposed of as a fuel product or as a feedstock for an additional process to recover usable carbon black which is not in the scope of this invention.

Examining the composition of the streams exiting the process reveals that no harmful chemicals are discharged to the environment in any form.

Examples of the more important features of this invention have been broadly outlined in order that the detailed description that follows may be better understood and so that the contributions which this invention provides to the art may be better appreciated. There are, of course, additional features of the invention which will be described herein and which will be included within the subject matter of the claims appended hereto.

BRIEF DESCRIPTION OF THE DRAWINGS

In the drawings:

FIG. 2 is a schematic representation of the feed preparation section of the process of this invention.

DETAILED DESCRIPTION OF THE INVENTION

Figure 1:
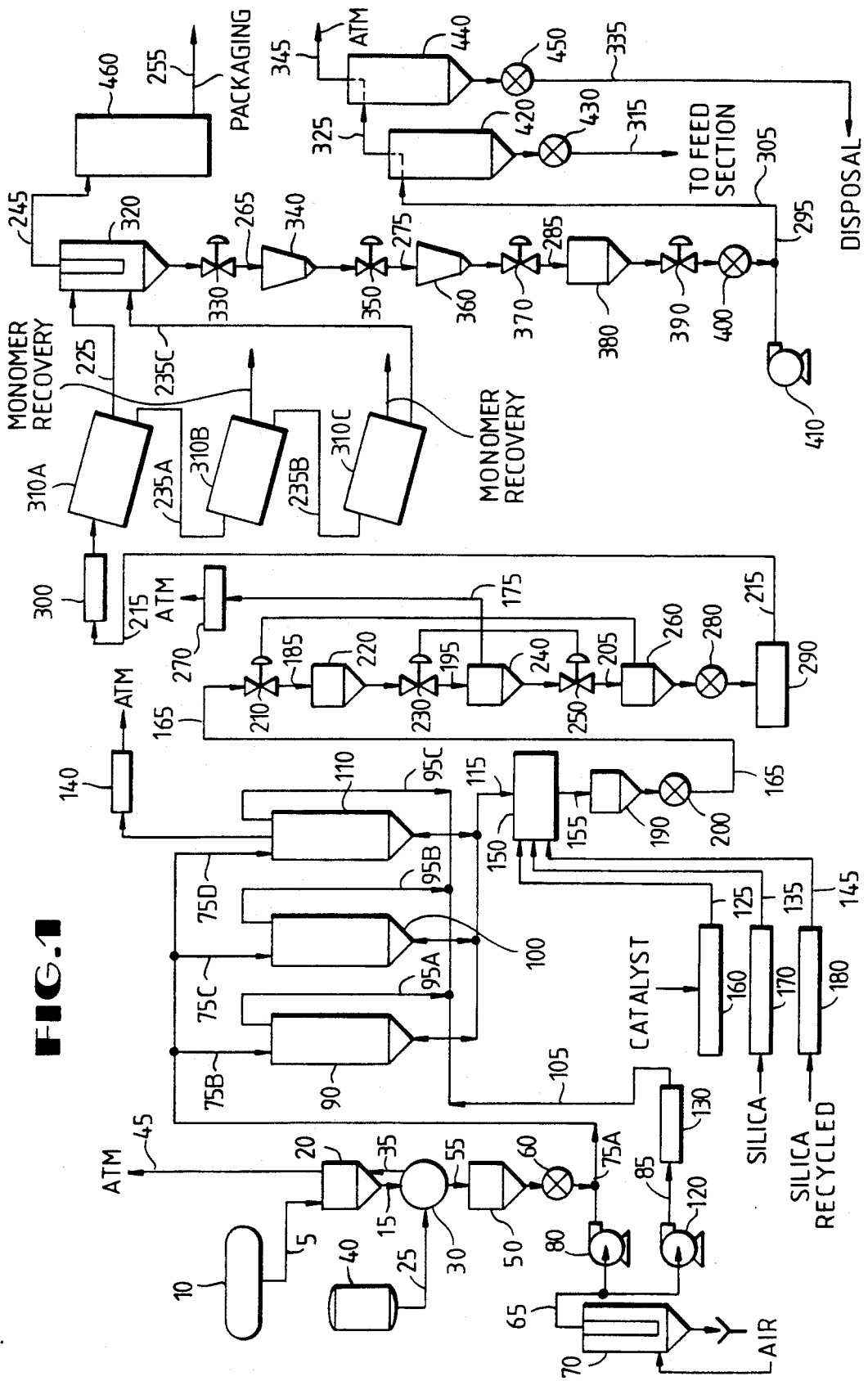
FIG. 1 is a schematic representation of the process of this invention.

Additional objects, features and advantages of the present invention will become apparent by referring to the following detailed description of the invention in connection with the accompanying drawings.

The basic processes for the depolymerization of used tire rubber and waste plastics is essentially identical. As a prelude to the depolymerization of used tires, and not a part of this invention, will be the collection of the used tires, shredding of the rubber into a small specified size and separation of the steel wire and fabric from the rubber particles. Removal of the steel wire prior to cryogenic grinding is preferred and can be accomplished off-site. It is expected that the carbon black in the feedstock rubber particles will be discharged from the depolymerization reactor as char, which will also contain ash and other residue, and will disposed of by other means either to be used as fuel or as a feedstock in a further process to recover usable carbon black. Because of the similarity in the process scheme for either used tire rubber or waste polymer feed the following will describe the processing of used tire rubber.

1. Feed Preparation Section

As illustrated in FIG. 2, shredded used tire rubber particles, about ⅛-3/16 inches in diameter, will be received from outside sources and conveyed by mechanical means, 10, and line 5 to the cryogenic grinder feed silo, 20, and fed via transfer line, 15, into the cryogenic grinder, 30, for size reduction. Cryogenic fluid, such as liquified nitrogen, will be fed from cryogenic storage tank, 40, through line 25 into the throat of the cryogenic grinder, 30, to embrittle the incoming rubber feedstock particles so that they can easily be fragmented by the cryogenic grinder, 30, into particles as small as −45 mesh U.S. sieve size. The pulverized rubber particles will drop via line 55 into the pulverized polymer receiver 50. The flashed cryogenic fluid will be vaporized during the cryogenic grinding operation. This cold gas will be fed countercurrent to the flow in stream 15 and through line 35 to the cryogenic grinder feed tank, up through the flow of incoming coarse rubber particles, cooling them until that stream is warmed and is vented to the atmosphere through line 45.

The pulverized rubber particles will be fed by rotating star feeder, 60, into pneumatic conveyor line 75 to the top of the ozone treatment silos, 90, 100 and 110. These silos will also serve as storage silos for the pulverized feedstock. The storage silos are large vertical cylindrical aluminum vessels capable of storing approximately 36 hours of pulverized rubber particles. Air will be filtered through bag filter 70, which will provide clean air to conveying blower 80, which conveys the pulverized rubber to the ozone treatment silos, and to the blower 120, serving the ozone generator 130, where a portion of the oxygen in the incoming air will be converted to gaseous ozone. The concentration of ozone in the gas stream 105, from the generator to the to the ozone treatment silos will approximate 3 parts per thousand by volume. The ozone containing stream will enter the bottom of silo 90 and pass upward through the bed of pulverized rubber particles, out the top of silo 90 and into the bottom of silo 100, up through the pulverized rubber particles in that silo, out the top of the silo 100 and into the bottom of silo 110, through the contents of silo 110 and out the top of silo 110 and through a hot copper oxide treater 140, which will convert the ozone to oxygen before it is vented to the atmosphere. The bottom feed streams to the ozone treatment silos will be manifolded and valved such that flow of the incoming ozone laden gas stream can be routed to the silos in any desired sequence, or through line 115 to the weighfeeder/blending station. The vented oxidizing streams from the top of the silos will be similarly manifolded. The residence time, approximately 36 hours, will give the ozone adequate time to fracture the chemical bonding of the pulverized vulcanized rubber particles causing deep stress cracking thereof.

Continuing with FIG. 2 the ozone treated pulverized particles are fed via line 115 to the weigh feeder/blending station. The ground finely divided rubber particles are discharged continuously onto a weigh scale/ribbon blender 150. Catalyst, fresh silica and recycled silica are dumped into hoppers 160, 170 and 180 respectively from whence they are batch fed to the weighfeeder/blender 150, on a batch basis where they are joined with the appropriate weight of pulverized treated rubber particles. Simultaneously weighed streams of catalyst, fresh silica and hot recycled silica are also fed into the ribbon blender 150 from weighfeeders 160, 170 and 180. After the batch of blended depolymerization reactor feed is weighed and blended it is discharged into the reaction section feed silo 190, via line 155. Hot silica, recovered from the depolymerization reactor and separated from other unreacted chemicals such as carbon black and sulfur, is recycled via weigh scale 180 to the ribbon blender 150.

2. Depolymerization Reaction Section

Figure 3:
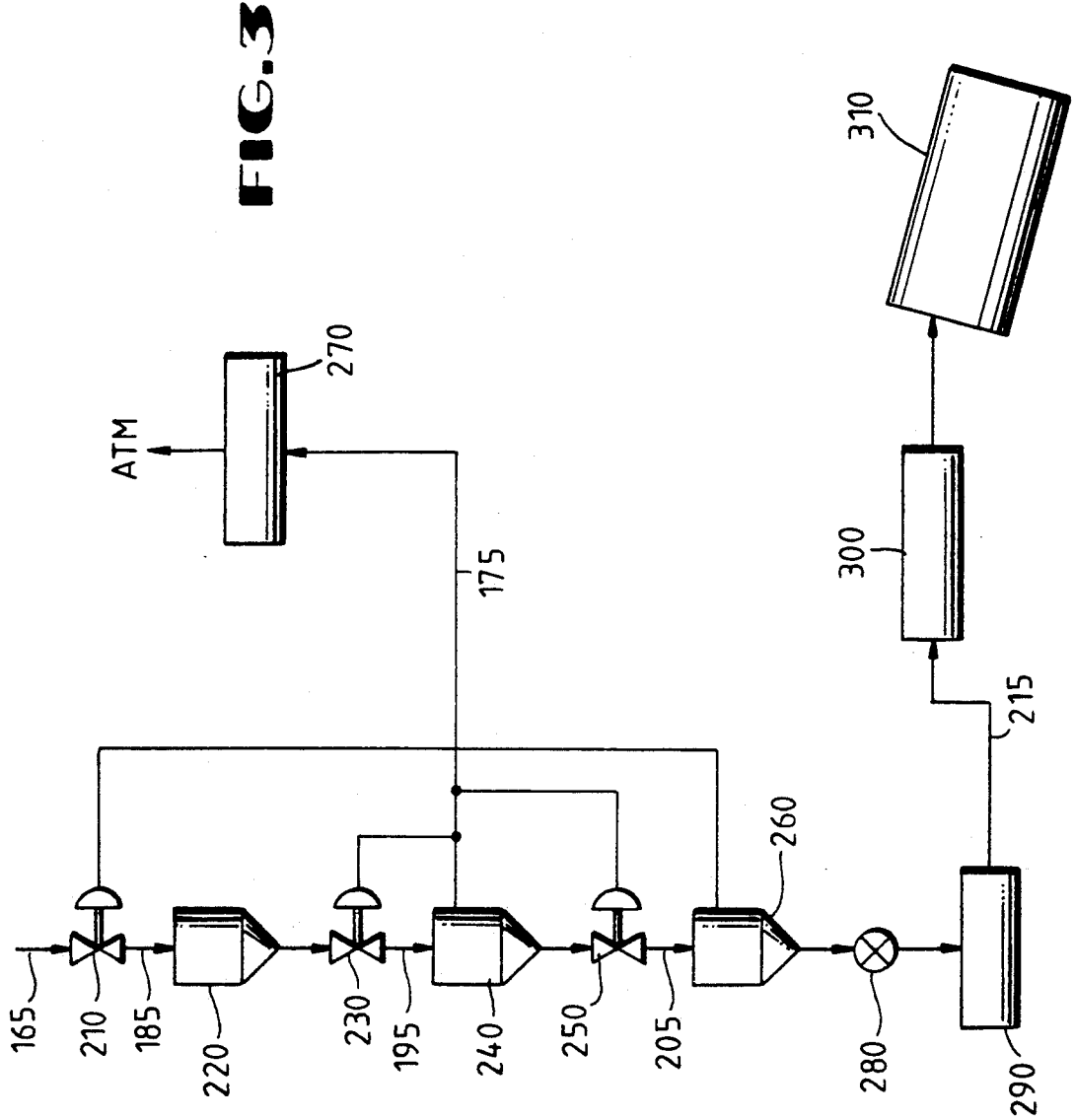
FIG. 3 is a schematic representation of the depolymerization reaction section of the process of this invention.
Figure 4:
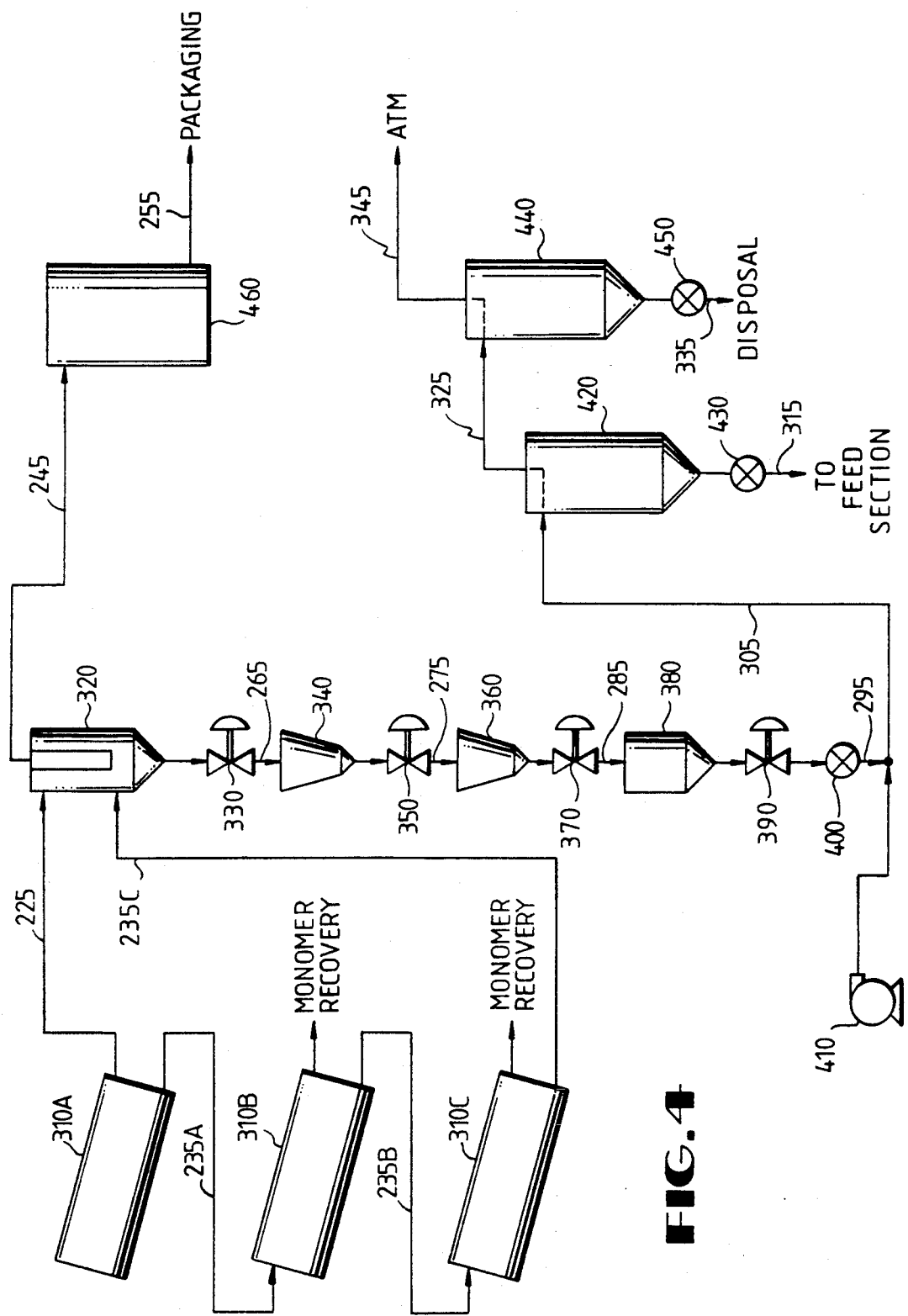
FIG. 4 is a schematic representation of the recovery section of the process of this invention.

FIG. 3 illustrates the Reaction Section, wherein the feed from FIG. 2 is depolymerized under vacuum and thermal conditions. In this section it will be necessary to provide a lock hopper system that will bring the rubber particles from atmospheric pressure to the partial vacuum condition of the reactor. The blended reactor feedstock will be fed continuously from the reaction section feed silo via rotating feeder 200 and fed via line 165, through ball valve 210 into the first feed lock hopper 220. With ball valves 210 and 230 closed, a vacuum is established in lock hopper 220 by the lock hopper vacuum system 270, through lock hopper vacuum lines 175. When the vacuum is established in hopper 220, ball valve 210 is opened and the finely divided particles are pulled from feed hopper 190 into hopper 220 by the vacuum in hopper 220. While hopper 220 is being filled ball valve 250 is closed and a vacuum is established in lock hopper 240. When the transfer to hopper 220 is complete ball valve 210 is closed and ball valve 230 is opened pulling the contents of hopper 220 into hopper 240 by vacuum. This technique of programmed operation of the ball valves and the establishing of vacuums in respective hoppers with the transfer of the feed from one evacuated hopper to another is repeated until the feed is in hopper 260. While hopper 260 was being evacuated and then filled, the cycle was being repeated, establishing a vacuum in hopper 220 and its subsequent filling with the next batch of feed stock. The feed in hopper 260 is fed through rotary star feeder onto hopper weigh feeder 290 which, in turn feeds sealed extruder 300 which continuously introduces the feed through the reactor end seal and into the rotating reactor 310. The depolymerization reactor is a custom designed elongated, slightly inclined rotating cylinder fitted with internal baffles which tumbles the feed as the reactor slowly rotates. The reactor is maintained at an elevated temperature, typically in the range of 300 to 550 deg F, and under a vacuum of approximately 27 inches of mercury. The reactor will be heated by external means, circulating a heat exchange fluid appropriate for maintaining the desired reaction temperature. The reactor vacuum will be maintained by the same vacuum systems servicing the vacuum distillation unit. As depolymerization takes place on the surface of the particulate the monomers evolving vaporize and are immediately removed from the reactor by the reactor and distillation vacuum unit to preclude their decomposing into less valuable products.

3. Recovery Section

After exiting reactor 310 via line 225 the gaseous monomers will pass through the bag filter 320, also under vacuum conditions, where they are separated from the entrained silica and carbon black. The separated solids will drop to the bottom of the bag filter unit where they will be joined by the unreacted by-products, silica, carbon black and sulfur. The gaseous monomers will flow via line 245 to the short path vacuum distillation unit, which is capable of operating at pressures as low as 1 millibar, where they will be separated and purified by distillation. The individual monomer steams will flow from the short path vacuum distillation unit 460 via line 255 to its packaging facilities, preparatory to shipment from the plant site. The silica and carbon black entrained in the monomer stream exiting the reactor will be joined by the stream of by-products of silica and carbon black and sulfur. These hot solids are continuously conveyed through line 235 to the discharge section of the bag filter 320. The solids must be removed from their vacuum regime without allowing air or other gases to flow into the bag filter and contaminate the recovered monomers. A second lock hopper system will be used to bring the by-products from their vacuum environment to atmospheric pressure. A solids recovery system consisting of a series of vessels operated in a programmed sequence will be used to move the solids from a vacuum to atmospheric pressure. Solids recovery vessels 340, 360 and 380 are arranged vertically to receive the flow of solids, controlled by the sequenced control valves 330, 350, 370 and 390. To preclude back flow of air into the bag filter 320, a lower vacuum than that in the bag filter 320, will be established in vessel 340, before control valve 330 is opened. When control valve 330 is opened the differential pressure between the bag filter 320, and solids recovery vessel 340 will cause the contents of the bag filter assembly to discharge into vessel 340. Valve 330 will close and vessel 340 will be pressurized with air to a nominal 25 psig. Control valve 350 will be opened and the differential pressure between vessel 340 and vessel 360 will cause the solids to flow into vessel 360. Programmed control valve 350 will close and the vacuum in vessel 340 will be reestablished prior to receiving another batch of solids from the bag filter 320. In a similar repeating sequence valves 370 and 390 will be operated to cause the solids to progressively flow through recovery vessels 360 and 380 and rotary feeder 400 into line 305 through which they are conveyed to cyclone separator 420. The cyclone separator will separate the hot silica, which is heavy, from the carbon black particles which are very light. The silica particles, contaminated with carbon black and sulfur, discharged in the cyclone underflow through rotary valve 430 and line 315, and will be reusable as recycle back to the feed preparation section. The overflow of the cyclone separator 420, containing the carbon black will be air conveyed to through line 325 to bag filter 440 where the carbon black will be recovered for utilization elsewhere. Complete separation of the carbon black, silica and sulfur is unnecessary. The filtered air from the bag filter will discharge to the atmosphere via line 345. In the event that a polymer or rubber contains multiple monomers, a series of rotating reactors will be provided, each operating at a different temperature as required to recover the monomers involved, the first reactor of the series operating at the lowest needed temperature and the last reactor operating at the highest temperature required to recover the last monomer. The vacuum streams from the reactors will pass through separate bag filters, to remove entrained solids and thence to separate short path vacuum distillation units. Solids recovery from multiple series reactors will be combined into a single recovery system. Recovery of the monomers from the distillation unit 460 will involve conventional condensing heat exchangers, compressors and storage systems. Conventional analytical techniques will be used to monitor the quality of the products. Further purification may involve conventional separation equipment.

What is claimed is:

1. A process for recovering a monomer from a vulcanized addition polymer feedstock formed from the monomer, comprising the steps of:
    (a) exposing the addition polymer feedstock to gaseous ozone under conditions sufficient to rupture chemical bonds formed during the vulcanization process of the addition polymer feedstock and thereby form one or more intermediate products;
    (b) mixing the intermediate products of step (a) with silica to form a mixture;
    (c) heating the mixture formed in step (b) to a temperature and for a time sufficient to depolymerize the addition polymer and form the monomer; and
    (d) removing the monomer following its formation from the mixture.

2. The process of claim 1 wherein the addition polymer feedstock is exposed to a mixture of gaseous ozone and air.

3. The process of claim 2 wherein the mixture of gaseous ozone and air comprises about 0.01 percent by weight of gaseous ozone.

4. The process of claim 1 wherein the addition polymer feedstock is exposed to gaseous ozone under conditions to rupture cross-linked bonds of the addition polymer feedstock.

5. The process of claim 1 wherein the addition polymer feedstock comprises particles ranging in size from about $-6$ to about $+25$ mesh.

6. The process of claim 1 wherein the mixture formed in step (b) is heated to a temperature of between about 250° C. and about 600° C.

7. The process of claim 1 wherein the mixture formed in step (b) is heated to a temperature of between about 450° C. and about 600° C.

8. The process of claim 1 wherein the mixture formed in step (b) is heated within a reaction zone having a pressure of from about 0.05 to about 0.25 atmospheres.

9. The process of claim 1 wherein the intermediate products of step (a) are mixed with silica and with a catalyst which is a salt selected from the group consisting of potassium carbonate, magnesium carbonate, calcium carbonate, sodium carbonate, and mixtures thereof.

10. The process of claim 1 wherein the intermediate products of step (a) are mixed with silica in a range from about a one to one ratio by volume to about a one to one-fourth ratio by volume.

11. The process of claim 1 wherein the addition polymer feedstock is rubber polymer recovered from used tires.

12. The process of claim 1 wherein the addition polymer feedstock is of polyolefin origin.

13. A process for the recovering more than one monomer from a vulcanized addition copolymer feedstock formed from multiple monomers, comprising the steps of:
    (a) exposing the addition copolymer feedstock to gaseous ozone under conditions sufficient to rupture chemical bonds formed during the vulcanization process of the addition copolymer feedstock and thereby form one or more intermediate products;
    (b) mixing the intermediate products of step (a) with silica to form a mixture;
    (c) consecutively heating within a series of close coupled reaction zones the mixture formed in step (b) to temperatures and for times sufficient to depolymerize the addition copolymer and form more than one monomer; and
    (d) removing each monomer following its formation from the mixture.

14. The process of claim 13 wherein the addition copolymer feedstock is exposed to a mixture of gaseous ozone and air.

15. The process of claim 14 wherein the mixture of gaseous ozone and air comprises about 0.01 percent by weight of gaseous ozone.

16. The process of claim 13 wherein the addition copolymer feedstock is exposed to gaseous ozone under conditions to rupture cross-linked bonds of the addition copolymer feedstock.

17. The process of claim 13 wherein the addition copolymer feedstock comprises particles ranging in size from about −6 to about +25 mesh.

18. The process of claim 13 wherein the mixture formed in step (b) is heated to temperatures of between about 250° C. and about 600° C.

19. The process of claim 13 wherein the mixture formed in step (b) is heated to temperatures of between about 450° C. and about 600° C.

20. The process of claim 13 wherein the mixture formed in step (b) is heated within reaction zones having pressures of from about 0.05 to about 0.25 atmospheres.

21. The process of claim 13 wherein the intermediate products of step (a) are mixed with silica and with a catalyst which is a salt selected from the group consisting of potassium carbonate, magnesium carbonate, calcium carbonate, sodium carbonate, and mixtures thereof.

22. The process of claim 13 wherein the intermediate products of step (a) are mixed with silica in a range from about a one to one ratio by volume to about a one to one-fourth ratio by volume.

23. The process of claim 13 wherein the addition copolymer feedstock is rubber copolymer recovered from used tires.

24. The process of claim 13 wherein the addition copolymer feedstock is of polyolefin origin.

* * * * *